United States Patent [19]

Hintze et al.

[11] Patent Number: 5,679,850
[45] Date of Patent: Oct. 21, 1997

[54] LITHIUM DIISAPROPYLAMIDE

[75] Inventors: Mark J. Hintze, Charlotte; Wen Jing Quan, Gastonia, both of N.C.

[73] Assignee: Cyprus Foote Mineral Company, Kings Mountain, N.C.

[21] Appl. No.: 735,229

[22] Filed: Oct. 22, 1996

[51] Int. Cl.$^6$ ................................................. C07C 209/90
[52] U.S. Cl. ................................................. 564/2; 564/463
[58] Field of Search ................................. 564/2, 463

[56] References Cited

U.S. PATENT DOCUMENTS

| | | |
|---|---|---|
| 4,595,779 | 6/1986 | Morrison et al. |
| 5,002,689 | 3/1991 | Mehta et al. |
| 5,320,774 | 6/1994 | Mehta et al. |
| 5,391,824 | 2/1995 | Smith ........................... 564/2 |
| 5,493,038 | 2/1996 | Hall et al. ................. 564/2 X |
| 5,574,197 | 11/1996 | Weiss et al. ............... 564/2 X |

*Primary Examiner*—Paul F. Shaver
*Attorney, Agent, or Firm*—Hudak & Shunk Co., L.P.A.

[57] ABSTRACT

Lithium diorganoamide compositions are prepared in ethers with an ether to diorganoamide mole ratio of from about 2.0 to about 5.0. These compositions have enough thermal stability generally due to the addition of stabilizers that the decomposition rate for lithium diorganoamide is less than 0.20% per day. Preferred stabilizers are LiBr, LiCl, LiI or Li-tert-butoxide, or combinations thereof. A preferred diorganoamide is lithium diisopropylamide.

21 Claims, No Drawings

LITHIUM DIISAPROPYLAMIDE

FIELD OF INVENTION

Lithium diorganoamide compositions are prepared in ether solvent by reacting diorganoamines with lithium metal in the presence of an electron acceptor and an ether solvent.

BACKGROUND OF THE INVENTION

The production of lithium diisopropylamide from the direct reaction of diisopropylamine with lithium metal in the presence of an electron acceptor, e.g., styrene, and an ether, e.g., diethyl ether, was described by M. T. Reetz and W. F. Maier in *Liebigs Annaten der Chemie*, 10, 1471 (1980). However the lithium diisopropylamide metalated the diethyl ether forming decomposition products of ethylene and lithium ethoxide. R. Morrison et al., in U. S. Pat. No. 4,595,779, combined the majority of the ether with the electron acceptor feed. The reaction vessel thus initially contained only the diorganoamine, (e.g., diisopropylamine) the hydrocarbon solvent, the lithium and the remaining balance of the ether. The drafters of the R. Morrison et al. reference limited the ether (tetrahydrofuran) to about 1 mole or less per mole of lithium diisopropylamide produced. The data taught that tetrahydrofuran: lithium organoamide ratios above 1:1 promote decomposition of the lithium diorganoamide.

U.S. Pat. Nos. 5,002,689 and 5,320,774 disclose bimetallic organoamides and particularly with one metal being lithium and the other being magnesium. These bimetallic organoamides are a substitute for lithium diorganoamides and according to Table I of the patents these bimetallic lithium magnesium diisopropylamides have superior stability against decomposition in the presence of tetrahydrofuran or other ethers. In both references column 2, lines 16–19 it is disclosed that lithium halide dissolved in the bimetallic organoamide increases solution stability of the bimetallic organoamide solutions. In U.S. Pat. No. 5,002,689 column 12, lines 14–44 the reference teaches that the mole ratio of THF: amide can be increased from the less than 1 value of U.S. Pat. No. 4,595,779 to values up to 1.9 and preferably from about 1.1 to about 1.6 to provide both for both solubility and stability of the organoamide.

SUMMARY OF THE INVENTION

It has been found that lithium diorganoamide compositions can be prepared from the reaction of diorganoamines with lithium metal in the presence of an electron acceptor and in the presence of an ether solvent. The amount of the ether solvent can be above 2.0 or 2.2 moles per mole of lithium diorganoamide if a stabilizer such as lithium bromide, lithium chloride, or lithium iodide in amounts from about 0.005 to about 0.50 moles or lithium tertiary butoxide in amounts from about 0.005 moles to about 0.05 moles per mole of lithium diorganoamide is present. The invention does not make a bimetallic diorganoamide and yet the lithium diorganoamide has unexpectedly good thermal stability.

DETAILED DESCRIPTION OF THE INVENTION

Lithium diorganoamide solutions can be prepared in an ether wherein the mole ratios of ether to lithium diorganoamide (LDA) are from desirably at least 2.0, 2.1, 2.2, 2.3 or 2.4, more desirably from about 2.0, 2.1, 2.2, 2.3 or 2.4 to about 5 and preferably from about 2.4 or 2.5 to about 3.5 or 4. A preferred ether is tetrahydrofuran and desirably at least 50 mole percent of the ether is tetrahydrofuran and more desirably at least 75 or 90 mole percent of the ether is tetrahydrofuran. Desirably said lithium diorganoamide solutions comprise at least 2.0, 2.2, 2.4 or 2.6 moles of tetrahydrofuran per mole of LDA. The above ratios of ether to lithium diorganoamide can alternatively be expresses as the same ratio to the diorganoamine reactant.

The lithium diorganoamide is prepared by a general reaction wherein the lithium metal, usually in a finely divided form, is dispersed in an organic solvent and the diorganoamine reactant is added thereto. A separate solution containing an electron acceptor, which can be for example, styrene or a conjugated unsaturated hydrocarbon, is added as a solution to the reaction mixture of lithium metal and diorganoamine. The ether solvent may be added with the electron acceptor as a mixture. Typically the lithium metal and the diorganoamine are present in a mole ratio of about 1:1 or a slight excess of either component can be present. The electron acceptor is generally present in a mole ratio of about 0.5 mole per mole of diorganoamine. If any reactants are present in a deficient amount they can limit the conversion of the other reactants. Often one or more of the reactants in a group consisting of lithium, diorganoamine, or electron acceptor are present in deficient amounts so that slight excess of one or more reactants are retained in the reaction product.

The diorganoamine reactant typically has a formula $R_1R_2NH$ wherein $R_1$ and $R_2$ are individually branched or linear alkyls having from 2 to 9 carbon atoms; a cycloalkyl having from about 3 to about 9 carbon atoms; a cycloalkenyl having from about 3 to about 9 carbon atoms; and an aryl or alkyl substituted aryl having from about 6 to about 10 carbon atoms. Preferably $R_1$ and $R_2$ are linear or branched alkyls or cycloalkyls having from about 3 to about 8 carbon atoms. A highly preferred diamine is diisopropylamine.

The lithium metal is a pure or essentially pure lithium metal from a conventional source. As indicated in the example the lithium used therein contained about 5 mole percent sodium. While lithium in the forms of rod, shot, wire, or powder can be used, the preferred form of lithium metal for reasons of handling and good reactivity are lithium powders or dispersions in a carrier. The lithium metal may contain small amounts of other metal such as sodium in amounts up to about 5 or 10 mole percent.

The ether solvent is preferably tetrahydrofuran because it is a commercially acceptable solvent and results in good yields of the lithium diorganoamide. Other ether solvents contain a total of from 2 to 12 carbon atoms and include diethyl ether, propyl ether, butyl ether, methyl isopropyl ether, tertiary butyl methyl ether and n-butyl methyl ether, tertiary amyl methyl ether, 2-methyl tetrahydrofuran, 2,2-dimethyl tetrahydrofuran, 2,2,5,5-tetramethyl tetrahydrofuran, tetrahydropyran, dioxanes and trimethylene oxide and other ethers reasonably resistant to being lithiated.

Other non-ether organic solvents can be used to provide a liquid reaction medium or a liquid carrier for the reactants or the reaction product from the above reaction. Examples of other solvents that can be used are linear and cyclic hydrocarbons having from about 5 to about 10 carbon atoms such as hexane, heptane, cyclopentane, methylcyclopentane, cyclohexane, methylcyclohexane, or aromatic solvents such as benzene, toluene, ethylbenzene, xylene and cumene. These hydrocarbon solvents are generally used in amounts from about 0.5, 0.75, 1.0, 1.2, 1.4 or 1.6 mole up to about 5 mole per mole of lithium diorganoamide, more desirably from about 1.0, 1.4, 1.5 or 1.6 mole to about 2 or 3 mole per mole of lithium diorganoamide. These values may also be expressed as per mole of diorganoamine. These hydrocarbon solvents can be selected to be easily removed at a later stage by volatilization or if less volatile organic solvents are used, they can be retained while other materials are moved from the reaction product by volatilization at reduced pressure. It has been found with the aromatic solvent ethyl benzene that unusual thermal stability against degradation without stabilizers was achieved. Thus it is desirable to have from about 1.2, 1.4 or 1.6 mole to about 2, 3, or 5 moles of an aromatic hydrocarbon solvent having from 6 to 15 carbon atoms in the lithium diorgano amide composition even when stabilizer is absent. More desirably the aromatic hydrocarbon solvent is ethylbenzene.

It is also desirable to optimize the amounts of hydrocarbon solvent and ether to get a thermally stable composition having a high concentration of lithium diorganoamide. The ratios of ether to diorganoamide above 2 recited herein allow the lithium diorganoamide concentration to vary from about 1.5 to about 3.0 molar and more desirably from about 1.5 or 1.6, or 1.75 to about 2.5 molar without insoluble lithium diorganoamide being generated. Higher active ingredient concentrations minimize shipping costs, storing costs, raw material costs, and solvent recycling costs. More dilute concentrations of lithium diorganoamide are achieved with higher amounts of hydrocarbon solvents.

The electron acceptor can be any conjugated unsaturated hydrocarbon that has the ability to accept an electron from the lithium metal, for example, styrene, methyl styrene, isoprene, butadiene, 2-methyl-1,3-pentadiene, divinylbenzene, etc. The mount of electron acceptor is not critical as long as it is not the limiting reagent. Amounts of electron acceptor are desirably from about 0.4 to about 0.7 mole per mole of diorganoamine and preferably from about 0.5 to about 0.6 mole per mole of diorganoamine.

A stabilizer is an important component to the lithium diorganoamide solutions as it may further stabilize the composition as the mole ratio of ether solvent to lithium diorganoamide is increased. Increased mole ratios of ether to lithium diorganoamide increases the solubility of the slightly polar lithium diorganoamide in the composition. As set forth in U.S. Pat. No. 4,595,779 column 5, first full paragraph in the prior art if insufficient ether solvent such as THF was present the lithium diorganoamides precipitated and if too much THF was present the lithium diorganoamide decomposed. It has been found that small amounts of lithium bromide, lithium chloride, lithium iodide, and lithium tertiary butoxide can stabilize lithium diorganoamide solutions wherein the mole ratio of ether to lithium diorganoamide is from about 2.0, 2.1 or 2.2 to about 5, more desirably from about 2.3, 2.4 or 2.5 to about 3.5 or 4. The amount of the lithium halide (e.g., bromide, chloride or iodide) desirable for stabilization is desirably from about 0.005 to about 0.40 or 0.50, more desirably from about 0.005, 0.01 or 0.02 to about 0.25 and preferably from about 0.005 to about 0.10 and most preferably from about 0.01 or 0.02 to about 0.05 moles per mole of lithium diorganoamide present. The amount of Li-butoxide is desirably from about 0.005 or 0.01 to about 0.04 or 0.05 moles per mole of lithium diorganoamide. The lithium butoxide can be added as lithium butoxide or preferably is generated in the reactor by adding butanol to lithium in the reactor prior to adding electron acceptor to said reactor. A preferred butanol is tert-butanol.

The reaction temperature is desirably controlled from about 35° to about 55° C. and is more desirably controlled between from about 40° to about 50° C. The lithium, organic solvent, and diorganoamine can be preheated to the reaction temperature ranges cited above prior to addition of the electron acceptor and the ether. The method of initiating the reaction has been found to be very crucial to both the reaction time and stability of the product. For example, if the most desirable reaction temperature is 45° C., then the amine is preheated to about 5° C. below the target temperature, i.e. 40°–42° C. Then the heat is removed and about 5% of the styrene/ether/LiX (X=Ci, Br, I, butoxide) solution is added at once into the vessel to initiate the reaction. The remainder of the styrene is added in less than 20 to 30 minutes. Cooling is applied as needed to maintain the target temperature; however, it is very desirable not to fall below the temperature at which the reaction was initiated. The reaction is typically continued after the addition of all the electron acceptor for a period of time until complete or nearly complete conversion of all the lithium and diorganoamine present in stoichiometric ratios has been achieved. The reaction time can vary from less than 1 hour to about 10 hours and is preferably for commercial reasons conducted in from about 2 to about 5 hours. The final concentration of lithium diorganoamide is desirably from about 1 to about 2.5 moles per liter and is preferably from about 1.5 to about 2 moles per liter.

It is desirable that the lithium diorganoamide solutions have good thermal stability so that the concentration thereof does not change substantially on aging. Using the teachings disclosed herein thermal stabilities of less than 0.5%, less than 0.4 or 0.3%, and less than 0.2% loss in activity per day are readily achievable when stored at 23°±2° C. for 30 days at a 2 molar solution concentration. In fact thermal stabilities of less than 0.15% loss, less than 0.10% loss, and less than 0.05% loss per day are achievable as shown in the tables.

Residual unreacted lithium or unreacted diorganoamine can be present in the final reaction product. The residual unreacted lithium to the extent that it is insoluble can be removed by filtration and recycled. The unreacted diorganoamine can be present from about 0 to about 20 mole percent based upon the moles of starting diorganoamine, more desirably it is from about 2 to about 10 mole percent and preferably it is from about 4 to about 8 mole percent of the amount of starting diorganoamine. Excess lithium is usually added to the reactor due to the fact that lithium is consumed by side reactions with moisture and other impurities. Up to 5 or 20 mole percent lithium can generally be added in excess to compensate for side reactions which consume lithium.

The lithium diorganoamide compositions in an ether solvent are not the bimetallic organoamides of the prior art patents such as U.S. Pat. No. 5,002,689. Therefore the compositions are substantially free of Mg, Ca, Be, and Sr. "Substantially free" of these metals is defined as desirably less than 1 mole percent based on the total moles of metals in the composition, more desirably less than 0.5 mole percent, preferably less than 0.40 or 0.25 mole percent, or less than 0.2 or 0.1 mole percent, and most preferably less than 0.05 mole percent. More desirably the recited mole % of metals are based solely upon the metal in the diorganoamide. The metals are defined as an element that forms positive ions when its compounds are in solution and whose oxides form hydroxides rather than acids with water. Most of the metal in these compositions is desirably lithium with trace amounts of sodium. Thus the Mg, Ca, Be, and Sr is desirably a few ppm or less based on the lithium diorganoamide in the lithium diorganoamide composition.

The lithium diorganoamides compositions are useful as strong bases in the preparation of pharmaceuticals. The following examples illustrate how lithium diisopropylamide can be formed and stabilized with the stabilizers of this disclosure.

EXAMPLE I

A first 50 ml, 3-necked flask containing a Teflon™ stir bar and fitted with rubber septa was flame dried and flushed with argon while the flask cooled. Once cool, the flask was taken into a dry box and 0.32 g (45 mmol) of Li metal dispersion was weighed into the flask. The flask was removed from the dry box and connected to an argon bubbler. To the flask was added 10 ml of hexane that had been dried over Na and distilled and 5.6 ml (40 mmol) of diisopropylamine that had been dried over $CaH_2$ and distilled. At this point the flask was fitted with a thermometer and the contents of the flask were heated to 40° C. with stirring.

0.17 g of LiBr (2 mmol) was weighed into a second flame dried flask that had been transferred to the dry box. The second flask was fitted with a septa and removed from the dry box. The lithium bromide was then dissolved in 9.8 ml of tetrahydrofuran (THF) (120 mmol) and 2.8 ml styrene (25 mmol). This solution was then drawn into a syringe and added dropwise to the first flask at 40° C. The addition was at such a rate that the temperature was maintained within the narrow range of 45°±2° C. and took approximately 20 minutes to complete. The temperature was then maintained at 45° C. for three hours (approximately 90% complete reaction according to $^1$H NMR). The reaction mixture was then filtered through a fitted glass filter, resulting in a clear, straw colored solution.

The procedure of Example 1 was used to create samples as listed in Tables 1–6 varying the conditions specified. The moles of carrier solvent, THF, and stabilizer are per mole of lithium diorganoamine. The electron acceptor was a conventional one used in conventional amounts. The stabilities were measured for the number of days specified when stored at 23°±2° C. and the value in parentheses in the tables under stabilities are the average loss in activity per day. The hydrocarbon solvent used makes a difference in thermal stability. The effect is most dramatic with ethyl benzene where the solution free of stabilizers has very low thermal degradation.

TABLE 1

| Sample | Cyclohexane Carrier moles | THF moles | LiBr moles | Temp(°C.) /Time (hr.) | Conversion % | Stabilities days/(loss) |
|---|---|---|---|---|---|---|
| A | 1.15 | 3 | 0.05 | 45/4 | 92 | 20d(.22%) |
| B | 2.3 | 3 | 0.05 | 45/5 | 91.7 | 35d(.05%) |
| C | 2.3 | 3 | 0 | 45/2.5 | 94 | 31d(.10%) |
| D | 2.3 | 2.5 | 0 | 45/2.5 | 94 | 31d(.06%) |
| E | 2.3 | 2.5 | 0.05 | 45–50/5.5 | 92 | 35d(.04%) |

In Table 1, the first two entries differ only in the amount of carrier solvent (cyclohexane) being used. On going from 1.15 mole to 2.3 mole of cyclohexane per mole of diorganoamine, it is clear that the daily stability has dramatically increased by approximately a factor of four. In effect, the higher amount of hydrocarbon carrier solvent used in the process is stabilizing the LDA. This is a new observation. Now, on going to the third entry in Table 1 in which 2.3 mole of cyclohexane is still being used but no LiBr is used, the stability has decreased by a factor of two. So there is a cumulative effect between the hydrocarbon solvent and LiBr. Both are contributing to the next stabilization of the LDA in solution.

The fourth and fifth entries of Table 1 demonstrate the impact of reducing the THF to 2.5 equivalents. At this level of THF the LiBr has little if any impact on the stability of the LDA. However, the LDA still benefits from the stabilizing effect of the 2.3 mole of cyclohexane versus 1.15 mole.

TABLE 2

| Sample | Heptane Carrier moles | THF moles | LiBr moles | Temp(°C.) /Time (hr.) | Conversion % | Stabilities days/(loss) |
|---|---|---|---|---|---|---|
| F | 0.9 | 3 | 0.05 | 45/4 | 92.6 | 32d(.14%) |
| G | 1.8 | 3 | 0.05 | 45/3.5 | 93.4 | 33d(.06%) |
| H | 1.8 | 3 | 0 | 45–50/2.5 | 94 | 33d(.11%) |
| I | 1.8 | 2.5 | 0 | 45–50/2.5 | 94 | 33d(.08%) |
| J | 1.8 | 2.5 | 0.05 | 45–50/4.5 | 93.4 | 33d(.10%) |

Table 2 shows the results when heptane is used as the carrier solvent. Again, looking at the first two entries one can see the effect of going from 0.9 mole to 1.8 mole of heptane. Once again there is a dramatic increase in the stability of the LDA at the higher volume of heptane, paralleling the results from cyclohexane. As in the case of cyclohexane, removing the LiBr (entry 3), results in a decrease in the stability of the LDA by a factor of two. So, the same cumulative effect is observed in heptane as cyclohexane.

Entries four and five are solutions with 2.5 equivalents of THF and 0 and 0.05 equivalents respectively of LiBr. Here again, the LiBr contributes little to the stability of the LDA at these lower THF levels, but the positive impact of the higher volume of heptane is still evident.

TABLE 3

| Sample | Hexane Carrier moles | THF moles | LiCl moles | Temp(°C.) /Time (hr.) | Conversion % | Stabilities day(loss) |
|---|---|---|---|---|---|---|
| 5/13 | 2 | 3 | 0.05 | 45/4.5 | 85 | 28d(.06%) |

From this point forward, we assume about 1 mole of a hydrocarbon carrier solvent will always be less stable than about 2 mole of the same solvent. Therefore, the entry in Table 3 simply demonstrates that LiCl has a stabilizing effect just as LiBr does on LDA when the THF:LDA ratio is 3 or more.

TABLE 4

| Sample | Hexane Carrier Solv. moles | THF moles | tert-BuOH moles | Temp(°C.) /Time (hr.) | Conversion % | Stabilities day(loss) |
|---|---|---|---|---|---|---|
| L | 2 | 3 | .02 in situ | 45/3.5 | 92.6 | 30d(.06%) |
| M | 2 | 3 | .02 in situ | 45/2.5 | 95 | 29d(.10%) |
| N | 2 | 3 | .02 after rxn | 45/5 | 94.3 | 32d(.65%) |
| O | 2 | 3 | .05 in situ | 45/4.5 | 87 | 29(.73%) |
| P | 2 | 3 | .052 in situ | 45/2.5 | 96 | 30(.61%) |
| Q | 2 | 3 | .06 after rxn | 45/5 | 94.3 | 32(.63%) |
| R | 2 | 3 | 0 | 45/5 | 94.3 | 32(.51%) |

Table 4 contains both positive and negative results from adding tert-butanol. First, there was a marked difference between the first two entries of this Table 4 and the third. The in situ generation of the t-BuOLi via addition of t-BuOH prior to the generation of LDA showed both reduced reaction times and stabilized solutions. However, the third entry in which the t-BuOH was added after the LDA had been generated appeared to actually destabilize the LDA solution. Concentrations of t-BuOH higher than 0.05, whether generated in situ or after the LDA has been made all destabilized the LDA solutions.

TABLE 5

| Sample | Ethyl Benzene Carrier moles | THF moles | LiBr moles | Temp(°C.) /Time (hr.) | Conversion % | Stabilities day(loss) |
|---|---|---|---|---|---|---|
| S | 1 | 3 | 0.05 | 45/4 | 89 | 32d(.17%) |
| T | 2 | 3 | 0.05 | 45/4 | 92 | 27d(.10%) |
| U | 2 | 3 | 0 | 45–50/2 | 93.5 | 31d(.06%) |
| V | 2 | 2.5 | 0 | 45–50/2 | 93.5 | 31d(0%) |
| W | 2 | 2 | 0 | 45/3.5 | 93.5 | 25d(.04%) |
| X | 2 | 2 | 0.05 | 45/4 | 94 | 25d(0%) |
| Y | 2 | 2.5 | 0.05 | 48/4.5 | 91.7 | 35d(.05%) |
| Z | 2 | 2.5 | 0.05 | 50/3.5 | 93.4 | 34d(.07%) |
| A1 | 2 | 2.5 | 0.05 | 54/3 | 95.2 | 35d(.05%) |

To test the stability of LDA in an aromatic hydrocarbon solvent, it was made in ethyl benzene since this is the reduced product of the styrene. The first two entries in Table 5 show that the stabilizing effect of a higher amount of carrier solvent is present in aromatic solvents just as it was in aliphatic case.

Interestingly, the stability of the LDA seems to be insensitive to the presence or absence of LiBr in these experiments. LDA is stable in ethyl benzene.

TABLE 6

| Sample | Hexane Carrier moles | THF moles | LiBr moles | Temp(°C.) /Time (hr.) | Conversion % | Ave. Stabilities (loss) |
|---|---|---|---|---|---|---|
| A2 | 2 | 3 | 0 | 45/3.5 | 83 | 41(.54%) |
| A3 | 2 | 3 | .05 | 45/4.5 | 83 | 41(.10%) |

LiBr in hexane shows the expected stabilizing effect on the LDA. In addition, while the average decomposition rate is reported as 0.1% per day at 41 days, at 26 days it was measured at 0.06% per day, which can be more directly compared to prior art.

Finally, the $^1$H NMR data demonstrates convincingly that the LDA is undergoing complexation with the LiBr. As the LiBr concentration is increased over the range of 0 to 9 equivalents, the LDA signal systematically moves upfield. Decomposition rates were then calculated by the relative increase of diisopropylamine in the solution. There was no evidence of imine formation that could potentially occur from elimination of LiH from LDA. Authentic samples of the imine from another source were used to evaluate whether detection of the imine, if present, would occur.

While in accordance with the patent statutes the best mode and preferred embodiment has been set forth, the scope of the invention is not limited thereto, but rather by the scope of the attached claims.

What is claimed is:
1. A lithium diorganoamide composition, comprising:

a) lithium diorganoamide of the formula

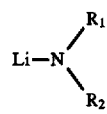

where $R_1$ and $R_2$ are individually linear or branched alkyl groups having from 2 to 9 carbon atoms or, cycloalkyl or cycloalkenyl groups having from 3 to 9 carbon atoms, or aryl or alkyl substituted aryl of from 6 to 10 carbon atoms,
b) at least 2.0 moles of a ether solvent per mole of said lithium diorganoamide, and
c) at least one stabilizer for said lithium diorganoamide comprising LiBr, LiCl, or LiI in an amount from about 0.01 to about 0.50 moles per mole of said lithium diorganoamide or Li-tert-butoxide in an amount from 0.005 to about 0.05 mole per mole of said lithium diorganoamide, and
wherein said lithium diorganoamide composition is substantially free of Mg, Ca, Sr, and Ba.

2. A lithium diorganoamide composition according to claim 1, wherein at least 2.1 moles of ether solvent is present per mole of said lithium diorganoamide and said lithium diorganoamide composition when prepared as a 2 molar solution is sufficiently temperature stable that it loses on average less than 0.2% of its activity per day when stored at 23°±2° C. for 30 days.

3. A lithium diorganoamide composition according to claim 1, having less than 0.5 mole percent of total Mg, Ca, Sr and Ba based on the total metals in said lithium diorganoamide, and wherein at least 2.2 moles of ether solvent is present per mole of said lithium diorganoamide.

4. A lithium diorganoamide composition according to claim 3, wherein at least 50 mole percent of said ether is tetrahydrofuran.

5. A lithium diorganoamide composition according to claim 3, wherein said lithium diorganoamide is lithium diisopropylamide and said total Mg, Ca, Sr, and Ba metals are less than 0.1 mole percent of the total metals in said lithium diorganoamide.

6. A lithium diorganoamide composition according to claim 4, wherein said lithium diorganoamide is lithium diisopropylamide and said total Mg, Ca, Sr, and Ba metals are less than 0.1 mole percent of the total metals in said lithium diorganoamide.

7. A lithium diorganoamide composition according to claim 6, having from about 2.5 to about 3.5 moles of tetrahydrofuran per mole of lithium diisopropylamide.

8. A lithium diorganoamide composition according to claim 7, wherein said stabilizer comprises from about 0.01 to about 0.05 moles of LiBr per mole of diorganoamide.

9. A lithium diorganoamide composition according to claim 8, wherein the composition loses less than 0.1% of its activity per day when stored at 23°±2° C. for 30 days.

10. A lithium diorganoamide composition according to claim 7, wherein said stabilizer is from about 0.01 to about 0.05 moles of lithium tert-butoxide per mole of lithium diorganoamide.

11. A lithium diorganoamide composition according to claim 4, wherein said composition loses on average less than 0.15% of its activity per day when stored at 23°±2° C. for 30 days.

12. A process for preparing a lithium diorganoamide composition, comprising:
providing a mixture of lithium metal and a diorganoamine, adding to said mixture a feed solution comprising an electron acceptor with a stabilizer while maintaining the temperature of said lithium metal and diorganoamine at from about 35° to about 55° C. to react said lithium with said diorganoamine to produce lithium diorganoamide, said feed solution optionally comprising an ether, with the proviso that from about 2.0 to about 5.0 moles of ether is added prior to or during said reaction per mole of said lithium diorganoamide, said stabilizer being from about 0.01 to about 0.25 moles of LiBr, LiCl, or LiI, or from about 0.005 to about 0.05 moles of Li-butoxide, or combinations thereof per mole of said lithium diorganoamide, said lithium diorganoamide being substantially free of Mg, Ca, Ba, and Sr based on the total moles of metal, and said lithium diorganoamide when prepared as a 2 molar solution being sufficiently temperature stable that it loses on average less than 0.20% of its activity per day when stored at 23°±2° C. for 30 days.

13. A process according to claim 12, wherein said ether is at least 50 mole percent tetrahydrofuran.

14. A process according to claim 13, wherein said stabilizer is from about 0.01 to about 0.05 moles of LiBr or LiCl per mole of said lithium diorganoamide and wherein said ether is from about 2.2 to about 3.5 moles per mole of said lithium diorganoamide.

15. A process according to claim 14, wherein said total Mg, Ca, Ba, and Sr is less than 0.1 mole percent of the total moles of metal.

16. A process according to claim 15, wherein the lithium diorganoamide composition loses on average less than 0.10% of its activity per day when stored at 23°±2° C. for 30 days and said lithium diorganoamide comprises lithium diisopropyl amide.

17. A process according to claim 13, wherein said stabilizer is from about 0.005 to about 0.04 moles of lithium-tert-butoxide per mole of said lithium diorganoamide.

18. A lithium diorganoamide composition, comprising;
the reaction product of:
a) a diorganoamine of the formula

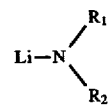

where $R^1$ and $R^2$ are individually linear or branched alkyl groups having from 2 to 9 carbon atoms, or cycloalkyl or cycloalkenyl groups having from 3 to 9 carbon atoms, or aryl or alkyl-substituted aryl having from about 6 to about 10 carbon atoms, b) an electron acceptor, c) lithium metal in the presence of from about 2.0 to about 5.0 moles of ether per mole of diorganoamine, and d) from about 0.5 to about 5 moles of at least one hydrocarbon solvent per mole of diorganoamine.

wherein said reaction product is substantially free of Mg, Ca, Sr, and Ba;

wherein said composition further includes from about 0.01 to about 0.25 moles of LiBr LiCl, or LiI, or from about 0.005 to about 0.05 moles of Li-butoxide, or combinations thereof per mole of lithium diorganoamide; and wherein said lithium diorganoamide loses less than 0.2% of its activity per day when stored at 23°±2° C. for 30 days.

19. A lithium diorganoamide according to claim 18, wherein said ether is from about 2.5 to about 5 moles per mole of said diorganoamine and is at least 0.5 mole percent tetrahydrofuran, and said composition has less than 0.1 mole percent of total Mg, Ca, Sr, and Ba based on the total metals of said lithium diorganoamide.

20. A lithium diorganoamide solution, comprising;
a) lithium diorganoamide of the formula

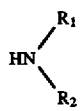

where $R_1$ and $R_2$ are individually linear or branched alkyl groups having from 2 to 9 carbon atoms or cycloalkyl or cycloalkenyl groups having from 3 to 9 carbon atoms, or aryl or alkyl substituted aryl having from 6 to 10 carbon atoms, b) at least 2.0 moles of a ether solvent per mole of said lithium diorganoamide, and c) at least one mole of an aromatic hydrocarbon solvent per mole of lithium diorganoamide, wherein said lithium diorganoamide loses on average less than 0.20% of its activity per day when stored at 23°±2° C. for 30 days, and wherein said reaction product is substantially free of Mg, Ca, Sr, and Ba.

21. A lithium diorganoamide solution according to claim 20, wherein said ether solvent is from about 2.2 to about 4 moles of said lithium diorganoamide, wherein said lithium diorganoamide is lithium diisopropylamide, said loss on average of activity per day is less than 0.10%, and said total Mg, Ca, Sr, and Ba metals are less than 0.5 mole percent of the total metals of said lithium diorganoamide.

* * * * *

UNITED STATES PATENT AND TRADEMARK OFFICE
CERTIFICATE OF CORRECTION

PATENT NO. : 5,679,850
DATED      : 10/21/97
INVENTOR(S): Mark J. Hintze and Wen Jing Quan It is certified that error appears in the above-indentified patent and that said Letters Patent is hereby corrected as shown below:

On the title page, in the title and column 1, line 1:

delete the first occurrence of "a" in "diisapropylamide" and inserting in its place --o--

Signed and Sealed this

Sixth Day of January, 1998

Attest:

Attesting Officer

BRUCE LEHMAN

Commissioner of Patents and Trademarks